United States Patent [19]

May

[11] Plant 5,010

[45] Mar. 22, 1983

[54] CHRYSANTHEMUM PLANT

[76] Inventor: Earl T. May, 2021 Sheridan Rd., Encinitas, Calif. 92024

[21] Appl. No.: 303,865

[22] Filed: Sep. 21, 1981

[51] Int. Cl.[3] ..... A01H 5/00

[52] U.S. Cl. ..... Plt./80

[58] Field of Search ..... Plt./80

*Primary Examiner*—James R. Feyrer

*Attorney, Agent, or Firm*—James R. Cypher

[57] ABSTRACT

The present invention relates to a new and distinct cultivar of Chrysanthemum Plant distinguished from its parent, as well as any other variety known to me, by its darker flower color, an earlier display of bud color, an overall flower response which is three to four days later, and a more coarse flower form due to lateral petal roll and notched petal tips.

1 Drawing Figure

BACKGROUND OF THE INVENTION

This invention relates to a new and distinct variety of chrysanthemum plant which is a sport of the cultivar Bravo, an unpatented commercial variety.

This sport was discovered and selected from a flowering of Bravo in my commercial greenhouses in Encinitas, Calif. in 1976 because of its distinctly darker, pleasing color. The distinguishing characteristics which are outstanding in the new cultivar and which distinguish it from its parent are as follows:

1. It has a darker flower color,
2. It shows bud color earlier than its parent,
3. Its overall flower response is three to four days later than its parent, and
4. It has more coarse flower form due to lateral petal roll and notched petal tips.

Asexual reproduction and flowerings of this new cultivar by cuttings was performed at Encinitas and Fremont, Calif. in commercial greenhouses. The new cultivar was found to retain its distinctive characteristics as listed herein through successive propagations.

BRIEF DESCRIPTION OF THE DRAWING

The accompanying color photograph illustrates the color of the flower and foliage as accurately as possible by photographic means. The new cultivar (C.S. 1069) appears on the right and its parent Bravo on the left.

DETAILED DESCRIPTION OF THE DRAWING

The following is a detailed description of the new chrysanthemum plant of the present invention. The color terminology used in the following is in accordance with The Royal Horticultural Society Colour Chart.

The parentage of the new chrysanthemum plant is as follows: Sport of the unpatented commercial cultivar Bravo.

The classification of the new variety is as follows:

*Botanical.*—*Chrysanthemum morifolium,* Ramat.

*Commercial.*—Pinch Pot Disbud.

The following detailed botanical description is based on observations made on Aug. 16, 1978 from plants grown inside my commercial greenhouse in Encinitas, Calif.

The height of plant and flower and foliage size established as an average using standard commercial cultural practices and the recommended "Medium" treatment of long day control as known in the industry: three to four weeks long days; plants were pinched and pruned to three leads. The data provided accurately characterizes the sport in question. Data collected from subsequent flowering trials may deviate slightly from the stated values, but the deviations will be within the range expected from varying environmental and cultural conditions. The form of the plant is Herbaceous and it grows in a vigorous semi-upright branching manner. The following table compares the new cultivar with its parent Bravo.

TABLE OF COMPARISON

| | New Cultivar | Bravo |
|---|---|---|
| PLANT: | | |
| Height | 30.48 cm | 30.48 cm |
| Response | 8½ weeks | 8 weeks |
| FOLIAGE: | | |
| Color - Upper side | 139 A | 139 A |
| Lower side | 137 B | 137 B |
| Size: | Length 7.62 cm × 5.08 cm width | Length 7.62 cm × 5.08 cm width |
| Quantity | Numerous | Numerous |
| Shape | Obvate lobed | Obvate lobed |
| Texture | Coarse | Coarse |
| Ribs and Veins | Prominent | Prominent |
| Margins | Moderately indented | Moderately indented |
| Serration | Moderate | Moderate |
| Stipules | Moderate | Moderate |
| BLOOM: | | |
| Size | 9.53 cm | 9.53 cm |
| Borne | Singly on disbudded stems | Singly on disbudded stems stems |
| Stem Strength | Strong | Strong |
| Form | Decorative | Decorative |
| Color: | | |
| Bud | 71 A | 64 A |
| Center | 65 D with broad streaks of 62 C | 8 D with 181 D discoloration |
| Upper side | 67 A fading 62 C–D along margins and apex | Areas of 65 C and 73 B |
| Lower side | 62 D with 65 A along bottom of keel | 62 D |
| Tonality 64 C | 62 B | |
| PETALS: | | |
| Texture | Smooth | Smooth |
| Appearance & Form | Similar to Bravo except a rudimentary appendage at the distal end of the tube is sometimes seen on florets; more notched than Bravo with a | Mostly open at base, some are closed forming a partial tube, flat shallow keel tapering to a blunt petal tip |

TABLE OF COMPARISON-continued

| | New Cultivar | Bravo |
|---|---|---|
| | longitudinal reflex. | with a slight reverse roll of the petal edges. |
| Arrangement | Composite, whorled on a single receptacle | Composite, whorled on a single receptacle |
| Persistence | Resist shattering | Resist shattering |
| Fragrance | Typical chrysanthemum | Typical Chrysanthemum |
| REPRODUCTION ORGANS: | | |
| Stamen | 0–5 | 0–5 |
| Pollen | Scant | Scant |
| Arrangement | Clustered in center of flower | Clustered in center of flower |
| Styles | Present both ray & disc florets | Present both ray & disc florets |
| Length | Medium | Medium |
| Ovaries | At base of petal attached to receptacle | At base of petal attached to receptacle |

I claim:

1. A new and distinctive cultivar of chrysanthemum plant, substantially as herein described, and distinguished from its parent by a darker flower color, an earlier display of bud color and an overall flower response which is 3–4 days later, and a more coarse flower form due to lateral petal roll and/or rudimentary appendages — notched petal tips.

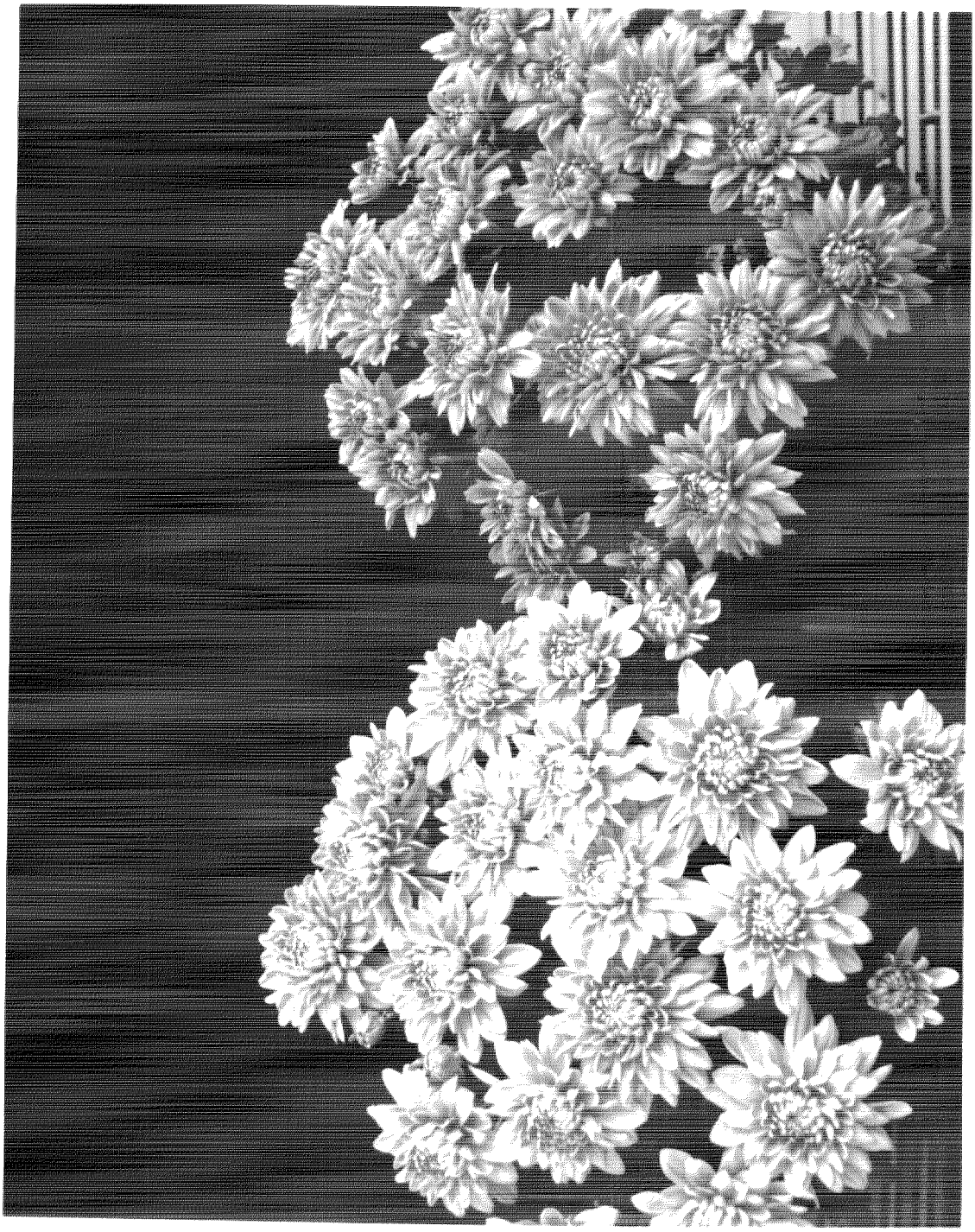

* * * * *